(12) United States Patent
Kawrykow et al.

(10) Patent No.: US 10,183,181 B2
(45) Date of Patent: Jan. 22, 2019

(54) ION CHAMBER FOR RADIATION MEASUREMENT

(71) Applicant: ViewRay Technologies, Inc., Oakwood Village, OH (US)

(72) Inventors: Iwan Kawrykow, Sofia (BG); Eyad Kishawi, San Carlos, CA (US)

(73) Assignee: VIEWRAY TECHNOLOGIES, INC., Oakwood Village, OH (US)

( * ) Notice: Subject to any disclaimer, the term of this patent is extended or adjusted under 35 U.S.C. 154(b) by 357 days.

(21) Appl. No.: 15/217,887

(22) Filed: Jul. 22, 2016

(65) Prior Publication Data

US 2017/0021198 A1    Jan. 26, 2017

Related U.S. Application Data

(60) Provisional application No. 62/195,743, filed on Jul. 22, 2015.

(51) Int. Cl.
*G01T 1/18* (2006.01)
*A61N 5/10* (2006.01)
(Continued)

(52) U.S. Cl.
CPC ............ *A61N 5/1071* (2013.01); *A61B 5/055* (2013.01); *A61N 5/1039* (2013.01); *A61N 5/1048* (2013.01); *A61N 5/1067* (2013.01); *A61N 5/1077* (2013.01); *G01T 1/185* (2013.01); *G01T 1/29* (2013.01); *G01T 1/2914* (2013.01); *A61N 2005/1055* (2013.01); *A61N 2005/1074* (2013.01); *A61N 2005/1094* (2013.01); *G01R 33/3806* (2013.01); *G01R 33/4808* (2013.01)

(58) Field of Classification Search
CPC ........... H01J 47/02; H01J 47/06; G01T 1/185; G01T 1/2935; G01T 1/18
See application file for complete search history.

(56) References Cited

U.S. PATENT DOCUMENTS 3,414,726 A    12/1968  Chameroy
3,852,610 A    12/1974  McIntyre
(Continued)

FOREIGN PATENT DOCUMENTS

| CA | 995827 A | 8/1976 |
|---|---|---|
| WO | WO-03/008986 A2 | 1/2003 |
| WO | WO-2008/006198 A1 | 1/2008 |

OTHER PUBLICATIONS

Lagendijk J. J. et al. "MRI guided radiotherapy: A MRI based linear accelerator." Radiotherapy & Oncology. vol. 56, No. Supplement 1. Sep. 2000. (Sep. 2000):S60-S61. XP008012866. 19th Annual Meeting of the European Society for Therapeutic Radiology and Oncology. Istanbul, Turkey; Sep. 19-23, 2000.
(Continued)

*Primary Examiner* — David Porta
*Assistant Examiner* — Mamadou Faye
(74) *Attorney, Agent, or Firm* — Pillsbury Winthrop Shaw Pittman LLP (57) ABSTRACT

An ion chamber has a chamber having an interior volume. There is a first electrode and a second electrode in the chamber and separated by a gap. A collector electrode is positioned between the first electrode and the second electrode. The collector electrode is shaped to occlude a portion of the first electrode from the second electrode.

20 Claims, 8 Drawing Sheets

(51) Int. Cl.
    *A61B 5/055*     (2006.01)
    *G01T 1/29*     (2006.01)
    *G01T 1/185*     (2006.01)
    *G01R 33/38*     (2006.01)
    *G01R 33/48*     (2006.01)

(56) References Cited

U.S. PATENT DOCUMENTS

| | | | |
|---|---|---|---|
| 3,879,612 A * | 4/1975 | Foster | G01T 3/006 |
| | | | 250/252.1 |
| 4,975,585 A | 12/1990 | Asai | |
| 5,693,947 A | 12/1997 | Morton | |
| 5,760,404 A | 6/1998 | Rannikko et al. | |

OTHER PUBLICATIONS

Tamada and Kose. "Two-Dimensional Compressed Sensing Using the Cross-sampling Approach for Low-Field MRI Systems." *IEEE Transactions on Medical Imaging.* vol. 33, No. 9. Sep. 2004. pp. 1905-1912.

* cited by examiner

ION CHAMBER FOR RADIATION MEASUREMENT

RELATED APPLICATION(S)

This application claims the benefit under 35 U.S.C. § 119(e) of U.S. Provisional Application No. 62/195,743, filed Jul. 22, 2015, titled "Ion Chamber for Radiation Measurement," which is hereby incorporated by reference.

TECHNICAL FIELD

The subject matter described herein relates to systems, methods and computer programs for magnetic resonance imaging and diagnostic and interventional applications associated therewith.

BACKGROUND

Magnetic resonance imaging (MRI), or nuclear magnetic resonance imaging, is a noninvasive imaging technique that uses the interaction between radio frequency pulses, a strong magnetic field (modified with weak gradient fields applied across it to localize and encode or decode phases and frequencies) and body tissue to obtain projections, spectral signals, and images of planes or volumes from within a patient's body. Magnetic resonance imaging is particularly helpful in the imaging of soft tissues and may be used for the diagnosis of disease.

Once diagnosed, radiation therapy treatment can be performed by directing a source of ionizing radiation, a linear accelerator (linac) for example, to deliver a radiation beam to a patient as part of the treatment plan. The output of a linac can be monitored, in part, by beam diagnostics that measure properties of the beam during treatment.

SUMMARY

In one aspect, an ion chamber has a chamber having an interior volume. There is a first electrode and a second electrode in the chamber and separated by a gap. A collector electrode is positioned between the first electrode and the second electrode. The collector electrode is shaped to occlude a portion of the first electrode from the second electrode.

In some variations there can be an entrance window with a thickness sufficient to stop nearly all electrons from an upstream linear accelerator.

In yet other variations, the first electrode and the second electrode can be plates.

In yet other variations, there can be a number of collector electrodes positioned in a symmetrical pattern around an axis of the ion chamber. The collector electrodes can be four annular segments positioned in a single collecting plane covering an annular area parallel to the first electrode and the second electrode. The collector electrodes can also include an annular ring electrode positioned to cover an annular area parallel to the first electrode and the second electrode.

In yet other variations, the collector electrodes are rectangular plates. The collector electrodes can also be four wedge plates positioned in a single collecting plane covering a circular area centered on an axis of the ion chamber. The four wedge plates can be separated from each other by gaps with an area substantially smaller than the circular area.

In an interrelated aspect, a method includes filling an interior volume of an ion chamber with a gas. There is a first electrode and a second electrode in the chamber and separated by a gap. A collector electrode is positioned between the first electrode and the second electrode. The collector electrode is shaped to occlude a portion of the first electrode from the second electrode. A current detector measures a first current received from the collector electrode. The first current is representative of a first charge generated by collisions between a radiation beam and the gas in the ion chamber. The first charge corresponds to a first portion of the radiation beam aligned with the collector electrode. A programmable processor generates a radiation beam profile based on the first current and a shape and a position of the collector electrode.

In some variations, the method can include measuring, at the current detector, a second current received from the first electrode and the second electrode. The second current can be representative of a second charge generated by collisions between the beam and the gas in the ion chamber. The second charge can correspond to a second portion of the radiation beam that is not aligned with the collector electrode. A radiation beam profile normalization can be determined based on the second current. A normalized radiation beam flux can be generated based on the first current and the normalization.

In yet other variations, a current detector can measure currents corresponding to collector electrodes positioned in a symmetrical pattern around an axis of the ion chamber. A second beam profile can be generated based on currents received from the collector electrodes, shapes of the collector electrodes, and positions of the collector electrodes.

In yet other variations, a current detector can measure currents each corresponding to collector electrodes positioned in a symmetrical pattern around an axis of the ion chamber. A ratio of currents received at the plurality of collector electrodes can be calculated. A radiation beam energy can be calculated based on the ratio of currents.

In yet other variations, the ion chamber can be used to monitor the radiation beam energy during operation of a linear accelerator that generates a radiation beam through the ion chamber. When the radiation beam energy is outside of an allowable range operation of the linear accelerator can be ceased.

In yet other variations, an electric field or a magnetic field separate from a main MRI magnetic field can be applied, based on the beam profile, to move the beam profile to align the radiation beam with an axis of the ion chamber.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Ion chambers can be used to measure a current that is related to some physical quantity or source of current. The ion chamber described herein, for example, can receive a radiation beam from a radiation source that can be used to treat a patient. When the radiation source is a linac, for example, the radiation beam is made up of high energy photons. The radiation beam can enter the ion chamber where photons in the radiation beam can strike a gas in the ion chamber. These collisions can ionize the gas by collisional ionization. The ionized gas can then be collected by an appropriately biased collector and measured as a current by a current detector.

Generally, the amount of current is related to the beam flux. However, by localizing the collection area (in one or more locations in the ion chamber) localized measurements of the beam flux can be made. These localized measurements can provide information on radiation beam flux, beam alignment, symmetry, or other features of the radiation beam profile.

References to "electron beam" and "radiation beam" are intended only to distinguish each type of beam before conversion by the target. For example, the electron beam or radiation beam could be any type of ionizing radiation, such as proton beams, cobalt sources, and the like. Similarly, the radiation beam can be any type of ionizing radiation that can interact with the ion chamber as described herein. The radiation beam can be, for example, X-rays, gamma rays, protons, electrons, ions, or the like.

Figure 1:
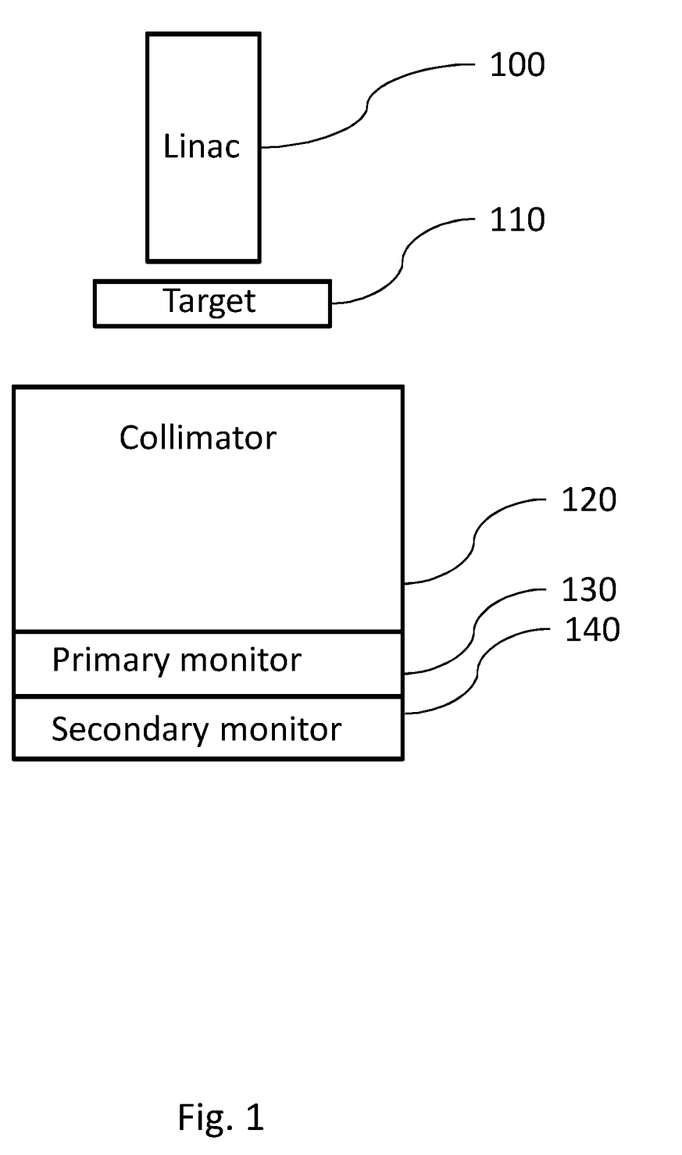
FIG. 1 is a diagram illustrating a simplified perspective view of an exemplary linear accelerator and ion chamber in accordance with certain aspects of the present disclosure.

FIG. 1 is a diagram illustrating a simplified perspective view of an exemplary linear accelerator and ion chamber in accordance with certain aspects of the present disclosure. For linear accelerators used in radiation therapy, two independent beam monitors can be implemented. An electron beam 10 can be emitted from the linac 100 and strike a target 110. The target 110 can convert the electron beam 10 to a photon beam used for patient treatment. There can be a primary monitor used for detection and regulation of the linear accelerator output, and a secondary monitor to serve as an independent check. These beam monitors can be placed in series downstream of a primary collimator 120, such as a multi-leaf collimator 120 (MLC). The ion chamber of the present disclosure can be used as either a primary monitor or secondary monitor.

If there is disagreement between the primary and secondary monitors, the system can fault and interrupt the patient treatment. In some cases, either the primary or secondary monitor, or both, can be used to check the symmetry or centering of the electron beam 10, as described in further detail herein.

Figure 2:
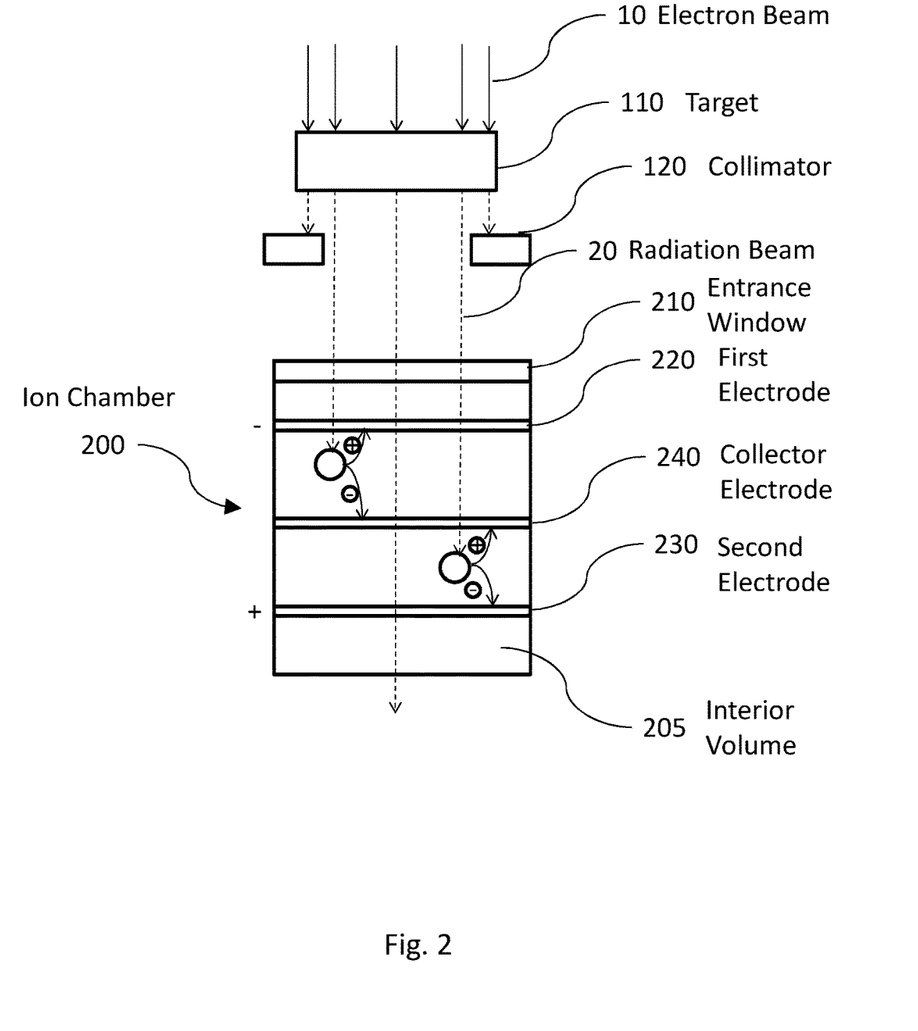
FIG. 2 is a diagram illustrating a simplified perspective view of an exemplary ion chamber in accordance with certain aspects of the present disclosure.

FIG. 2 is a diagram illustrating a simplified perspective view of an exemplary ion chamber 200 in accordance with certain aspects of the present disclosure. In one implementation, the ion chamber 200 can be a chamber with an interior volume 205 and an entrance window 210. Inside the ion chamber 200, there can be a first electrode 210 and a second electrode 230 separated by a gap. The ion chamber 200 can be filled with gas and that will at least partially ionize when a radiation beam 20 passes through the ion chamber 200. The first electrode 210 and second electrode 230 can be conducing plates held at a specified potential to generate an electric field in the ion chamber 200. In the example shown in FIG. 2, the first electrode 210 is at a negative potential and the second electrode 230 is a positive potential. When an ionization event occurs (shown by the open circles) an electron ejected from the now positively charged ion goes towards the second electrode 230 and the positively charged gas ion goes to the first electrode 210. Depending on where the gas is ionized, the collector electrode 240 can intercept and collect the charges, which can then be measured as a current by a current monitor. Also, some of the radiation beam 20 can pass through the ion chamber 200 without ionizing, as shown by the middle dashed arrow in FIG. 2.

The sign conventions shown in FIG. 2 are for illustrative purposes and should not be considered limiting. As used herein, the choice of which electrode is the first electrode 210 and the second electrode 230 is arbitrary, as is the direction of the applied electric field from the bias potentials placed on the electrodes.

The radiation beam 20 can enter the ion chamber 200 through the entrance window 210. Also, the entrance window 210 can prevent the entry of electrons into the ion chamber 200. The entrance window 210 can be, for example, the wall of the ion chamber 200, a filter or other material placed at or near the entrance of the ion chamber 200, or the like. For example, the entrance window 210 may be constructed with aluminum having a wall thickness of approximately 2 mm, 3 mm, 4 mm, 5 mm, 6 mm or 8 mm. In one implementation, the entrance window 210 can be made of 4 mm thick aluminum. In other implementations, a desired attenuation can be obtained with a thinner entrance window 210 combined with a filter and/or other materials designed to achieve the same attenuation. In yet other implementations, the thickness of entrance window 210 can sufficient to, in combination with the target 110 of the linac 100, stop all or nearly all electrons from entering the ion chamber 200, for example, electrons from an upstream linac 100, secondary electrons generated outside the ion chamber 200, or the like.

The overall thickness of the ion chamber 200 can be small to minimize the overall attenuation of the radiation beam 20 by the ion chamber 200. The ion chamber 200 thickness can be, for example, approximately 3 mm, 5 mm, 7 mm, or 9 mm.

A collector electrode 240 can be positioned between the first electrode 210 and the second electrode 230. The collector electrode 210 can be shaped to occlude a portion of the first electrode 210 from the second electrode 230. As used herein, "occlude" can refer to any interception of a radiation beam 20 by the collector electrode 240. For example, in FIG. 2, the plate forming the collector electrode 240 occludes the entire downstream electrode from the upstream electrode.

The charge collected on a collector electrode 240 can be measured by a trans-impedance or equivalent low-leakage amplifier. Current measurements can then be converted to an estimate of beam flux and/or dose through a calibration or comparison with a radiation treatment plan.

While some examples configurations of electrodes are given below, there can be any number of collector electrodes (and also the first electrode 210 and the second electrode 220), for example, 2, 3, 4, 6, 8, 10, or the like. Similarly, the electrodes can be other shapes besides those described in the specific examples below. For example, the collector electrodes (and also the first electrode 210 and the second electrode 220) can be rectangular, circular, hexagonal, or the like.

Figure 3:
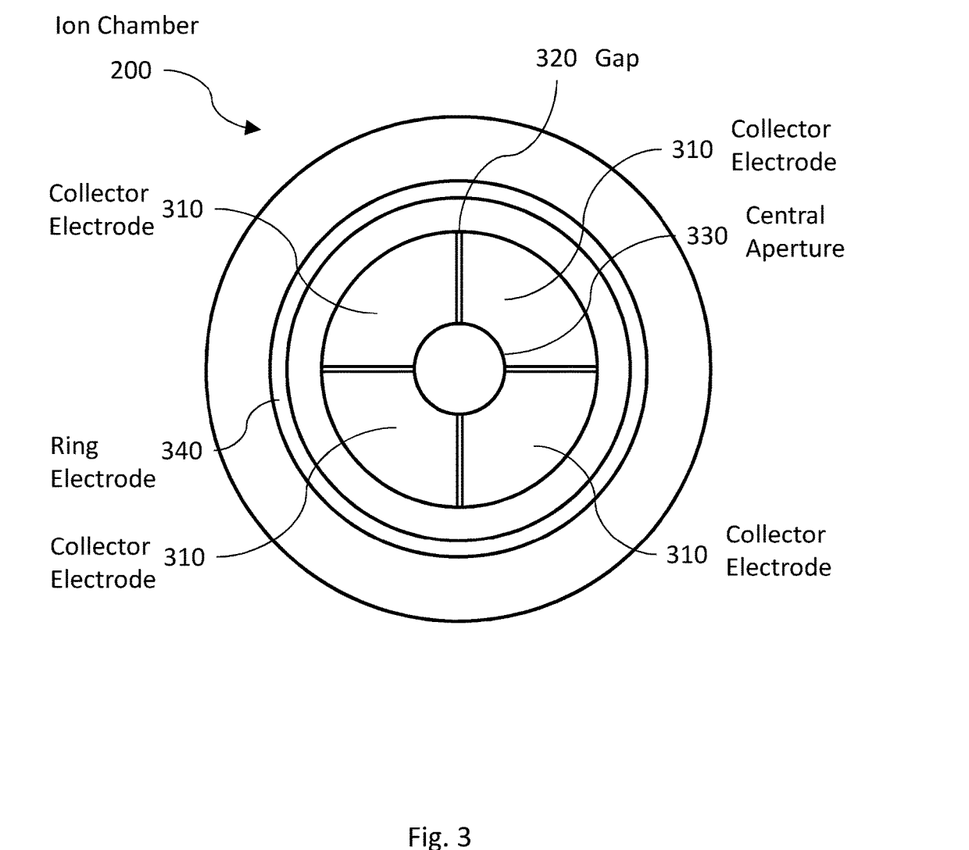
FIG. 3 is a diagram illustrating a simplified view of a first exemplary ion chamber electrode configuration in accordance with certain aspects of the present disclosure.

FIG. 3 is a diagram illustrating a simplified view of a first exemplary ion chamber 200 electrode configuration in accordance with certain aspects of the present disclosure. In alternative implementations, there can be multiple collector electrodes 310, and each collector electrode 310 can be connected to an independent current sensor. In this way, the beam flux corresponding only to the cross-sectional area of the individual collector electrodes 310 can be measured. As shown in FIG. 3, the collector electrodes 310 can be positioned in a symmetrical pattern around an axis, for example through the center of the ion chamber 200. In this example implementation, there are four collector electrodes 310. In particular, the four collector electrodes 310 can be shaped as four annular segments covering four quadrants of an annular area. The collector electrodes 310 can be in a single collecting plane to cover an annular area parallel to the first electrode 210 and the second electrode 230.

As shown in the implementation of FIG. 3, a central aperture 330 can be present in the assembled collector electrodes 310. At the central aperture 330, the collector electrodes 310 do not occlude the first electrode 210 (the upstream electrode) from the second electrode 230 (the downstream electrode).

In some implementations, there can also be an annular ring electrode 340 positioned to cover an annular area parallel to the first electrode 210 and the second electrode 230. The annular ring electrode 340 can be circular in shape, but can also be rectangular, hexagonal, or any other shape. The annular ring electrode 340 can also be separated into an arbitrary number of segments, for example 2, 4, or 8, similar to the four annular segments. The annular ring electrode 340 can be thin compared to its overall diameter, to provide a measure of beam flux at a known radius from the axis. In some implementations, the annular ring electrode 340 can be located near the periphery of the chamber.

Figure 4:
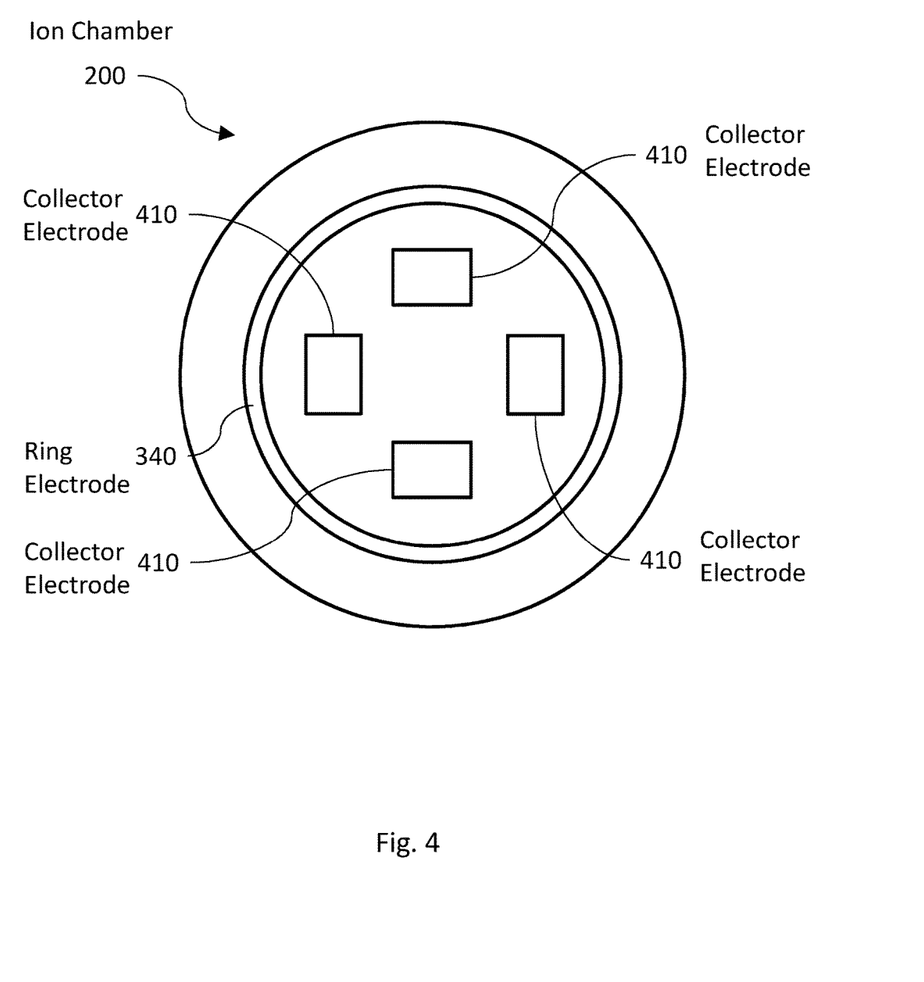
FIG. 4 is a diagram illustrating a simplified view of a second exemplary ion chamber electrode configuration in accordance with certain aspects of the present disclosure.

FIG. 4 is a diagram illustrating a simplified view of a second exemplary ion chamber 200 electrode configuration in accordance with certain aspects of the present disclosure. In another implementation, the collector electrodes 410 can be rectangular plates. The rectangular plates can be positioned in a symmetric pattern around the axis. In the implementation of FIG. 4, the reduced collection area can allow more of the radiation beam 20 to traverse the ion chamber 200 unimpeded. Also, the increased spacing between the collector electrodes 410 can reduce the likelihood of breakdown between them in the event that an excess of charge builds up on one or more of the collector electrodes 410.

Figure 5:
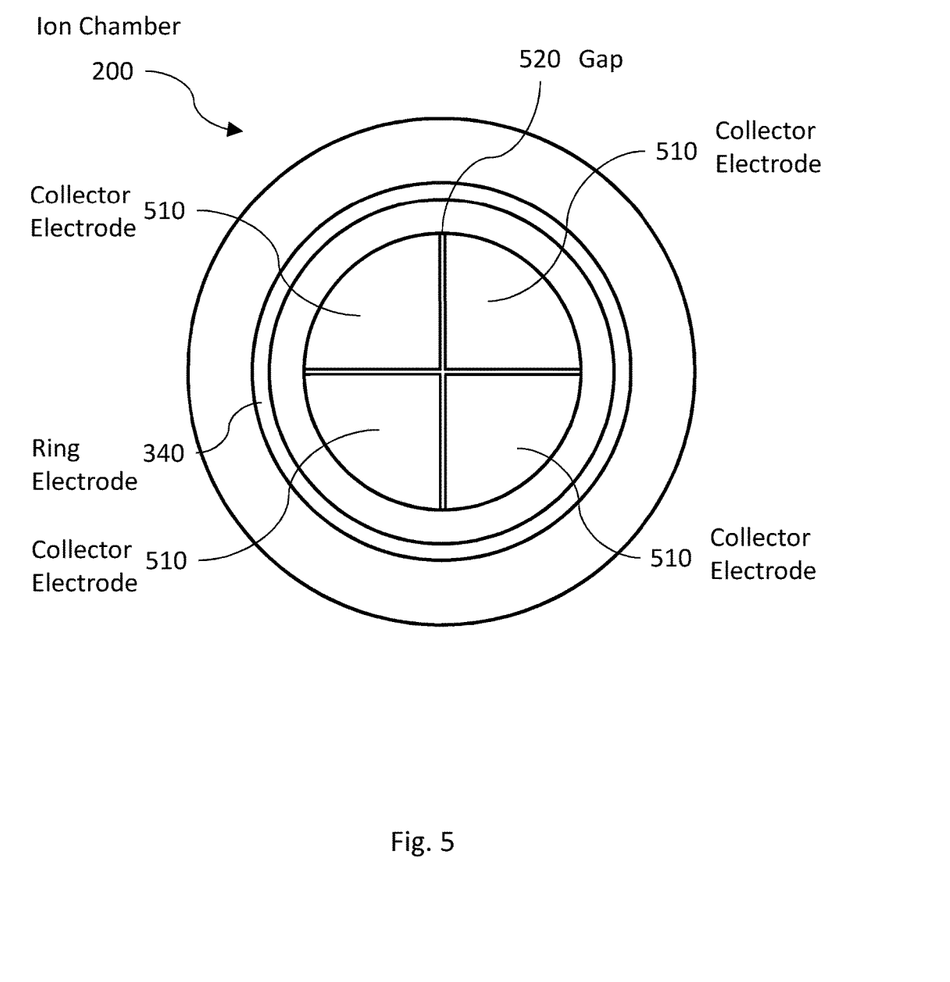
FIG. 5 is a diagram illustrating a simplified view of a third exemplary ion chamber electrode configuration in accordance with certain aspects of the present disclosure.

FIG. 5 is a diagram illustrating a simplified view of a third exemplary ion chamber 200 electrode configuration in accordance with certain aspects of the present disclosure. The implementation of FIG. 5 is similar to that shown in FIG. 3. The collector electrodes 510 here can be four wedge plates each positioned in a single collecting plane and covering a circular area centered on an axis of the ion chamber 200. The four wedge plates can be separated from each other by gaps with an area substantially smaller than the circular area. For example, the gap width can be, for example, 0.1 cm, 0.05, or 0.01 cm. Also, in this implementation, the collector electrodes 510 do not have a central aperture. Such a configuration can allow radiation beam flux measurements even when the radiation beam 20 is strongly peaked on-axis.

Figure 6:
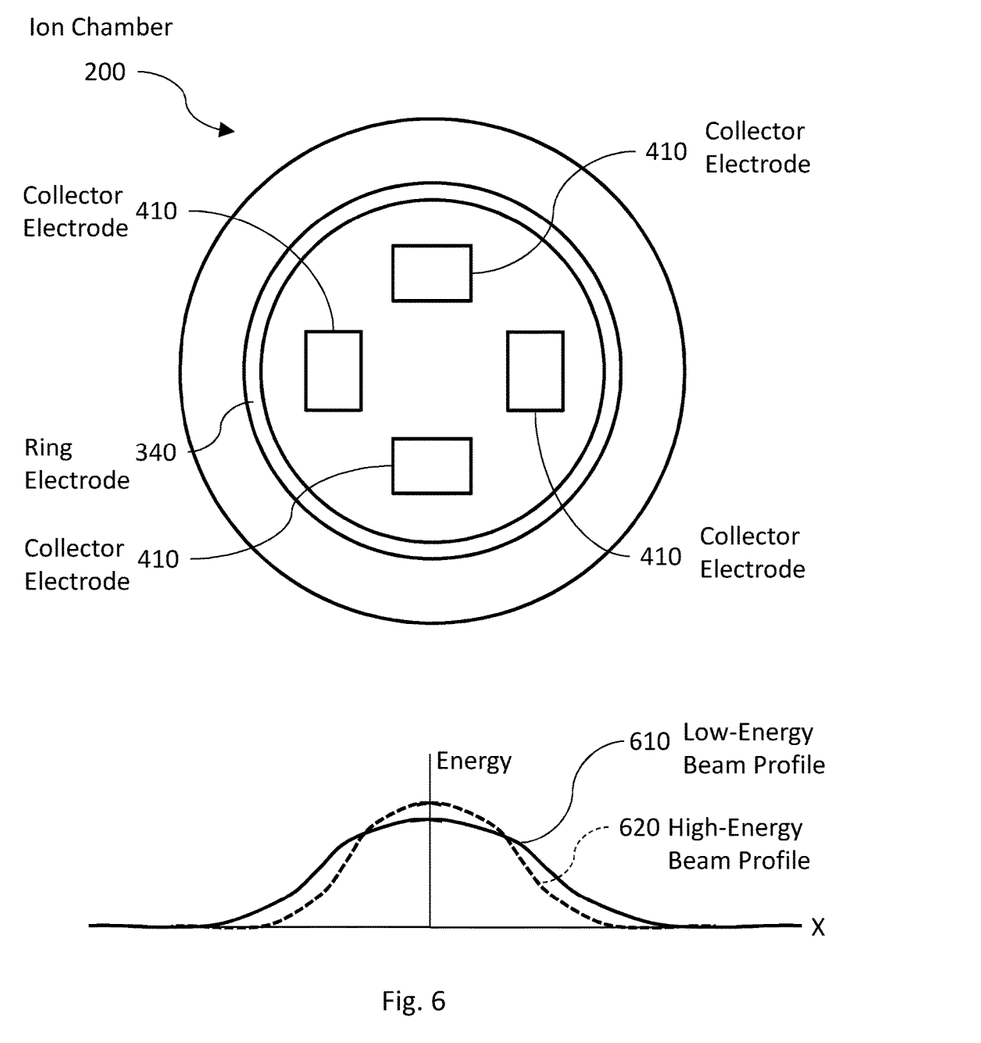
FIG. 6 is a diagram illustrating a simplified view of a ring electrode in an ion chamber used to measure beam profile symmetry in accordance with certain aspects of the present disclosure.

FIG. 6 is a diagram illustrating a simplified view of a ring electrode in an ion chamber 200 used to measure beam profile symmetry in accordance with certain aspects of the present disclosure. The implementations described herein can allow the measurement of, for example, total beam flux through the ion chamber 200, beam symmetry, beam symmetry, 2-D beam structure, and beam energy. The examples below are given also in reference to the configuration described in FIG. 4, but can also apply to other configurations as well, including, for example those shown in FIG. 3 and FIG. 5.

In some implementations, all or nearly all, of the radiation beam 20 can enter the ion chamber 200. This can occur when there is no collimator 120 or when the collimator 120 or MLC is configured to not block the radiation beam 20. With a known or assumed beam profile shape, for example, flat, Gaussian, or the like, the total current intercepted by the collector elements 410 will be proportional to the beam flux. It is not necessary that the radiation beam 20 be entirely unobstructed. For example, with an assumed beam profile and a known collection area (of the collector electrodes), an estimate of the beam flux into the ion chamber 200 can be determined.

Measurements of beam symmetry can be performed by measuring the current with different collector elements arranged in a symmetric pattern, for example as shown in FIGS. 3-6. If the beam is not symmetric, then different currents will be measured on the collector elements 410. While the radiation beam 20 could be adjusted to provide equal currents to the center electrodes, a configuration where the annular ring electrode 340 was segmented would likely measure different currents, revealing that the beam is asymmetric instead of merely misaligned.

As the number of collector elements increases, more features of the radiation beam 20 can be measured. For example, azimuthal asymmetries can be measured by differences in current at different collector electrodes 410 at the same radial distance from the axis.

As used herein, the collector electrodes that are inside the annular ring electrode 340 are also referred to as center electrodes 410. In one implementation, the center electrodes 410 can be used to measure beam symmetry, while the ring electrode(s) may be used as a baseline for overall beam energy measurement. In another implementation, the sum of the currents at the center electrodes 410 can also serve as an additional measure of the overall beam energy.

The energy of the radiation beam 20 can affect the shape of the radiation beam 20. For example, in some implementations, a radiation beam 20 can be broader at low energy than at a higher energy. This is illustrated in FIG. 6 by the two exemplary radiation beam flux profiles. In this example, the lower-energy beam profile 610 (solid curve) is broader than the higher energy beam profile 620 (dashed curve). In this example, assuming a constant radiation beam flux, the ratio of the current received at the center electrodes to the current received at the annular ring electrode 340 is a function of the radiation beam energy. When the radiation beam 20 is higher energy, the ratio will be larger, and when the radiation beam 20 is at a lower energy, the ratio will be smaller. In the specific example shown in FIG. 6, the ratio R can be expressed as $$R = \frac{\Sigma_1^4 i_n}{i_5}. \quad (1)$$

The numerator of (1) is the total current at the center electrodes and the denominator of (1) is total current at the annular ring electrode. With a calibration using the measured current at a known beam energy and beam profile, monitoring the ratio R can provide ongoing measurements of the radiation beam energy. When the ratio is outside an allowable range, the system can, for example, fault and stop operation, alert a user, or the like. Similar actions can also occur in response to measuring a beam asymmetry or misalignment, as described by the methods herein.

Figure 7:
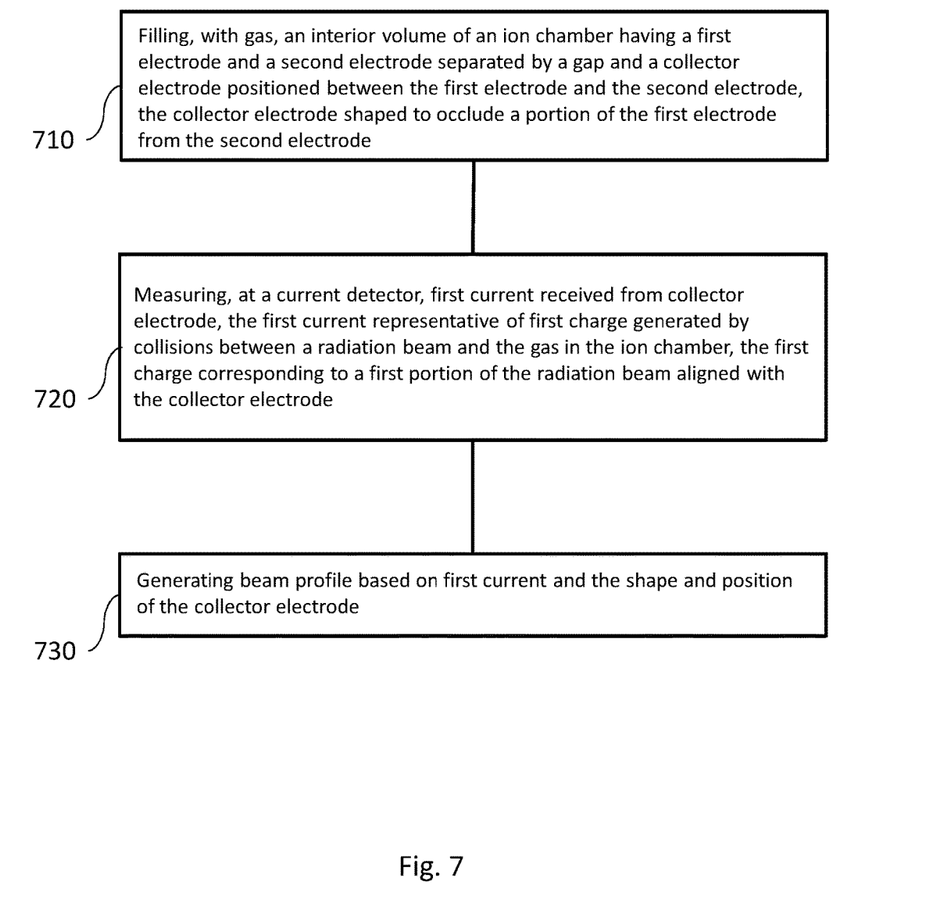
FIG. 7 is a simplified diagram for an exemplary method of measuring beam profile characteristics in accordance with certain aspects of the present disclosure.

FIG. 7 is a simplified diagram for an exemplary method of measuring beam profile characteristics in accordance with certain aspects of the present disclosure.

At 710, an interior volume of the ion chamber 200 can be filled with a gas. The ion chamber 200 can surround a first electrode 220 and a second electrode 230 separated by a gap and a collector electrode 240 positioned between the first electrode 220 and the second electrode 230, the collector electrode 240 shaped to occlude a portion of the first electrode 220 from the second electrode 230.

At 720, a current detector can measure a first current received from collector electrode 240. The first current can be representative of first charge generated by collisions between a radiation beam 20 and the gas. The first charge can correspond to a first portion of the radiation beam 20 aligned with the collector electrode 240.

At 730, beam profile can be generated based on first current and the shape and position of the collector electrode 240.

Figure 8:
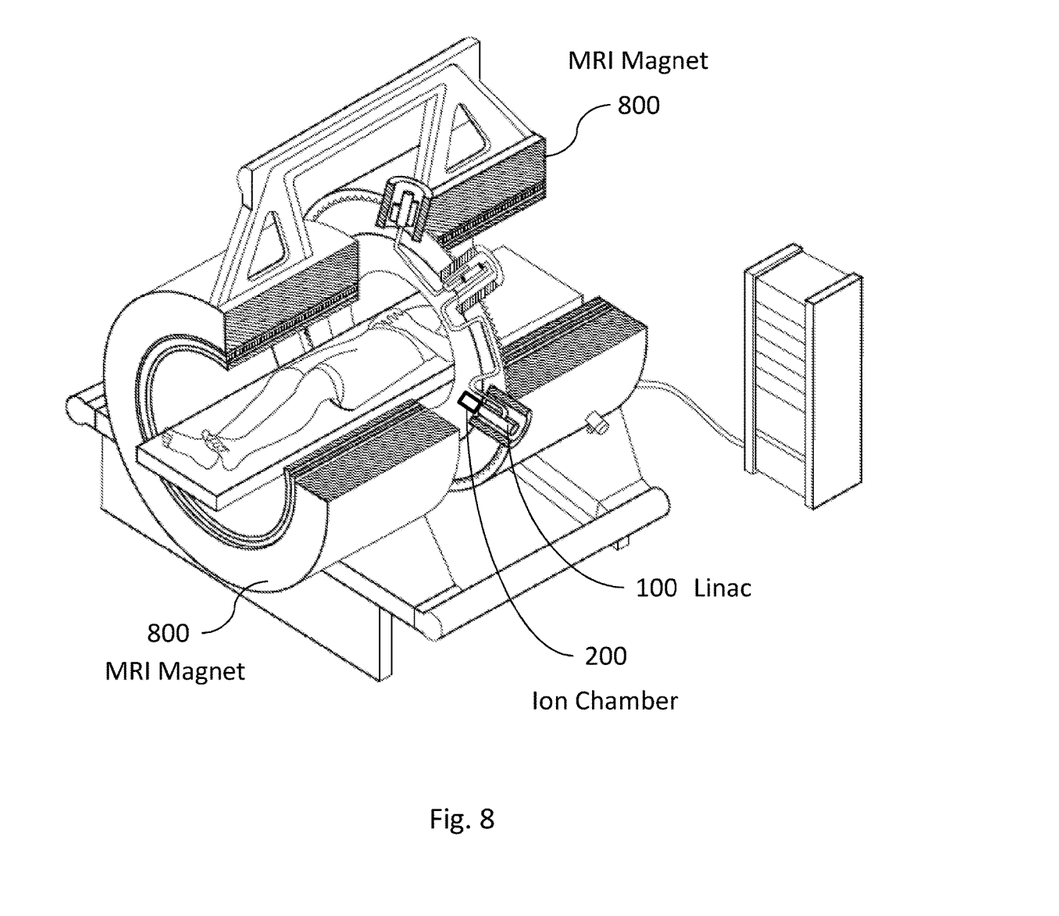
FIG. 8 is a diagram illustrating a simplified view of a combination MRI system and linac incorporating an ion chamber in accordance with certain aspects of the present disclosure.

FIG. 8 is a diagram illustrating a simplified view of a combination MRI system and linac 100 incorporating an ion chamber 200 in accordance with certain aspects of the present disclosure. The MRI magnets 800 can generate the magnetic field used for conducting magnetic resonance imaging. In the ion chamber 200, when measuring current at the collection elements, the main MRI magnetic field can introduce several sources of error.

When a symmetric arrangement of collector electrodes receives different currents, but the beam is symmetric, the electron beam 10 beam is likely not co-axial with the ion chamber 200. Misalignment or asymmetry can be compensated for by aligning the electron beam 10 from the linac 100 with magnetic coils or an electric field. The magnetic coils can be, for example, separate shimming coils positioned about the linac 100. The current in the magnetic coils can be adjusted to either reduce the MRI magnetic field locally in the linac 100 or to otherwise change the beam trajectory. Plates on either side of the electron beam 10 can also be used to provide an electrostatic potential to steer the electron beam 10 by varying an electric potential on the plates. In another implementation, magnetic shielding can be added to the linac 100 to reduce the effect of the MRI magnetic field on the electron beam 10. If the distortion cannot be fully eliminated, it can be measured and taken into account with a calibration as a function of magnetic field strength.

Another source of error can be deflection of electrons or ions by the magnetic field leaking into the ion chamber 200. Where in the absence of a magnetic field the trajectories of the ionized gas and electrons would be guided only by the electric potential at the collectors or the first or second electrodes, the MRI magnetic field can cause the trajectories can go to other locations in the ion chamber 200 and affect the measured current. In some implementations, this error can be corrected by magnetically shielding the ion chamber 200, or with a calibration to account for the changes when the MRI magnets are on. When the radiation beam 20 is properly aligned and the ion chamber 200 is sufficiently shielded, symmetric collector electrodes will receive the same current.

Although a few embodiments have been described in detail above, other modifications are possible. For example, the collector electrode shapes shown in FIG. 3-6 and described herein do not require the particular ordering, shapes, or positions shown to achieve desirable results.

The present disclosure contemplates that the calculations disclosed in the embodiments herein may be performed in a number of ways, applying the same concepts taught herein, and that such calculations are equivalent to the implementations disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. An ion chamber comprising:
   a chamber having an interior volume;
   a first electrode and a second electrode in the chamber and separated by a gap; and
   a collector electrode positioned between the first electrode and the second electrode, the collector electrode shaped to occlude a portion of the first electrode from the second electrode.

2. An ion chamber as in claim 1, further comprising an entrance window with a thickness sufficient to stop nearly all electrons from an upstream linear accelerator.

3. An ion chamber as in claim 1, wherein the first electrode and the second electrode are plates.

4. An ion chamber as in claim 1, further comprising a plurality of collector electrodes positioned in a symmetrical pattern around an axis of the ion chamber.

5. An ion chamber as in claim 4, wherein the plurality of collector electrodes comprises four annular segments positioned in a single collecting plane covering an annular area parallel to the first electrode and the second electrode.

6. An ion chamber as in claim 4, wherein the plurality of collector electrodes further comprise an annular ring electrode positioned to cover an annular area parallel to the first electrode and the second electrode.

7. An ion chamber as in claim 4, wherein the plurality of collector electrodes are rectangular plates.

8. An ion chamber as in claim 4, wherein the plurality of collector electrodes further comprise four wedge plates positioned in a single collecting plane covering a circular area centered on an axis of the ion chamber, wherein the four wedge plates are separated from each other by gaps with an area substantially smaller than the circular area.

9. A method comprising:
filling, with a gas, an interior volume of an ion chamber comprising:
  a first electrode and a second electrode separated by a gap; and
  a collector electrode positioned between the first electrode and the second electrode, the collector electrode shaped to occlude a portion of the first electrode from the second electrode;
measuring, at a current detector, a first current received from the collector electrode, the first current representative of a first charge generated by collisions between a radiation beam and the gas in the ion chamber, the first charge corresponding to a first portion of the radiation beam aligned with the collector electrode; and
generating, by at least one programmable processor, a radiation beam profile based on the first current and a shape and a position of the collector electrode.

10. A method as in claim 9, further comprising:
measuring, at the current detector, a second current received from the first electrode and the second electrode, the second current representative of a second charge generated by collisions between the beam and the gas in the ion chamber, the second charge corresponding to a second portion of the radiation beam that is not aligned with the collector electrode; and
determining, by the at least one programmable processor, a radiation beam profile normalization based on the second current; and
generating, by the at least on programmable processor, a normalized radiation beam flux based on the first current and the normalization.

11. A method as in claim 9, further comprising:
measuring, at the current detector, a plurality of currents each corresponding to a plurality of collector electrodes positioned in a symmetrical pattern around an axis of the ion chamber; and
generating, by the at least one programmable processor, a second beam profile based on a plurality of currents received from the plurality of collector electrodes, shapes of the plurality of collector electrodes, and positions of the plurality of collector electrodes.

12. A method as in claim 9, further comprising:
measuring, at the current detector, a plurality of currents each corresponding to a plurality of collector electrodes positioned in a symmetrical pattern around an axis of the ion chamber;
calculating, based on the plurality of currents, a ratio of currents received at the plurality of collector electrodes; and
calculating, based on the ratio of currents, a radiation beam energy.

13. A method as in claim 12, further comprising:
monitoring, with the ion chamber, the radiation beam energy during operation of a linear accelerator that generates a radiation beam through the ion chamber; and
ceasing operation of the linear accelerator when the radiation beam energy is outside of an allowable range.

14. A method as in claim 9, further comprising:
applying an electric field or a magnetic field separate from a main MRI magnetic field, based on the beam profile to move the beam profile to align the radiation beam with an axis of the ion chamber.

15. A computer program product comprising a non-transient, machine-readable medium storing instructions which, when executed by at least one programmable processor, cause the at least one programmable processor to perform operations comprising: measuring, at a current detector, a first current received from a collector electrode, positioned between a first electrode and a second electrode, the collector electrode shaped to occlude a portion of the first electrode from the second electrode, the first current representative of a first charge generated by collisions between a radiation beam and a gas in an ion chamber, the first charge corresponding to a first portion of the radiation beam aligned with the collector electrode; and generating, by the at least one programmable processor, a radiation beam profile based on the first current and a shape and a position of the collector electrode.

16. A computer program product as in claim 15, further comprising:
measuring, at the current detector, a second current received from the first electrode and the second electrode, the second current representative of a second charge generated by collisions between the beam and the gas in the ion chamber, the second charge corresponding to a second portion of the radiation beam that is not aligned with the collector electrode; and
determining, by the at least one programmable processor, a radiation beam profile normalization based on the second current; and
generating, by the at least one programmable processor, a normalized radiation beam flux based on the first current and the normalization.

17. A computer program product as in claim 15, further comprising:
measuring, at the current detector, a plurality of currents each corresponding to a plurality of collector electrodes positioned in a symmetrical pattern around an axis of the ion chamber; and
generating, by the at least one programmable processor, a second beam profile based on a plurality of currents received from the plurality of collector electrodes, shapes of the plurality of collector electrodes, and positions of the plurality of collector electrodes.

18. A computer program product as in claim 15, further comprising:
measuring, at the current detector, a plurality of currents each corresponding to a plurality of collector electrodes positioned in a symmetrical pattern around an axis of the ion chamber; and
calculating, based on the plurality of currents, a ratio of currents received at the plurality of collector electrodes; and
calculating, based on the ratio of currents, a radiation beam energy.

19. A computer program product as in claim 18, further comprising:
monitoring, with the ion chamber, the radiation beam energy during operation of a linear accelerator that generates a radiation beam directed through the ion chamber; and ceasing operation of the linear accelerator when the radiation beam energy is outside an allowable range.

20. A computer program product as in claim 15, further comprising:

applying an electric field or a magnetic field separate from a main MRI magnetic field, based on the radiation beam profile to, to align the radiation beam with an axis of the ion chamber.

* * * * *